US008715948B2

(12) United States Patent
Granville et al.

(10) Patent No.: US 8,715,948 B2
(45) Date of Patent: May 6, 2014

(54) GRANZYME A AND GRANZYME B DIAGNOSTICS

(71) Applicant: The University of British Columbia, Vancouver, CA (US)

(72) Inventors: David Granville, Port Coquitlam, CA (US); Rani Cruz, Vancouver, CA (US); Ciara Chamberlain, Vancouver, CA (US); Wendy Bolvin, Coquitlam, CA (US); Bruce McManus, Vancouver, CA (US)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 13/867,870

(22) Filed: Apr. 22, 2013

(65) Prior Publication Data

US 2013/0323749 A1  Dec. 5, 2013

Related U.S. Application Data

(62) Division of application No. 12/681,349, filed as application No. PCT/CA2008/001752 on Oct. 1, 2008, now Pat. No. 8,426,149.

(60) Provisional application No. 60/960,478, filed on Oct. 1, 2007, provisional application No. 60/996,138, filed on Nov. 2, 2007, provisional application No. 60/996,139, filed on Nov. 2, 2007.

(51) Int. Cl.
*G01N 31/00* (2006.01)
*G01N 33/53* (2006.01)
*G01N 33/543* (2006.01)

(52) U.S. Cl.
USPC ........ 435/7.21; 435/7.1; 435/287.9; 436/501; 436/518; 530/300; 530/350

(58) Field of Classification Search
CPC ............. G01N 2333/96436; G01N 2800/065; G01N 2800/10; G01N 33/68; G01N 33/6893
See application file for complete search history.

(56) References Cited

U.S. PATENT DOCUMENTS

| | | | |
|---|---|---|---|
| 6,699,486 B1 | 3/2004 | Bolla | |
| 8,426,149 B2 * | 4/2013 | Granville et al. | 435/7.21 |
| 2003/0148511 A1 | 8/2003 | Ashton-Rickardt | |
| 2004/0259172 A1 | 12/2004 | Christgau | |
| 2005/0208000 A1 | 9/2005 | Bernstein | |
| 2006/0019945 A1 | 1/2006 | Chapman | |
| 2011/0229546 A1 | 9/2011 | Granville | |
| 2012/0171144 A1 | 7/2012 | Granville | |

FOREIGN PATENT DOCUMENTS

| | | |
|---|---|---|
| EP | 0 580 859 A1 | 2/1994 |
| EP | 1 163 900 A1 | 12/2001 |
| EP | 1 281 396 A2 | 2/2003 |
| WO | 99/54737 A1 | 10/1999 |
| WO | 03/065987 A2 | 8/2003 |
| WO | 2004/067778 A2 | 8/2004 |
| WO | 2004/100889 A2 | 11/2004 |
| WO | 2007/036028 A1 | 4/2007 |
| WO | 2009/055934 A1 | 5/2009 |
| WO | 2012/076985 A2 | 6/2012 |

OTHER PUBLICATIONS

Accardo-Palumbo, A., et al., "The Level of Soluble Granzyme A Is Elevated in the Plasma and in the Vγ9/Vδ2 T Cell Culture Supernatants of Patients With Active Behcet's Disease," Clinical and Experimental Rheumatology 22(4 Suppl 34):S45-S49, Jul.-Aug. 2004.
Adiguzel, E., et al., "Collagens in the Progression and Complications of Atherosclerosis," Vascular Medicine 14(1):73-89, Feb. 2009.
Ang, L.S., et al., "Serpina3n Attenuates Granzyme B-Mediated Decorin Cleavage and Rupture in a Murine Model of Aortic Aneurysm," Cell Death & Disease 2(9):e209, Sep. 2011, 5 pages.
Banda, M.J., and Z. Werb, "Mouse Macrophage Elastase. Purification and Characterization as a Metalloproteinase," Biochemical Journal 193(2):589-605, Feb. 1981.
Barry, M., and R.C. Bleackley, "Cytotoxic T Lymphocytes: All Roads Lead to Death," Nature Reviews. Immunology 2(6):401-409, Jun. 2002.
Bird, C.H., et al., "Selective Regulation of Apoptosis: The Cytotoxic Lymphocyte Serpin Proteinase Inhibitor 9 Protects Against Granzyme B-Mediated Apoptosis Without Perturbing the Fas Cell Death Pathway," Molecular and Cellular Biology 18(11):6387-6398, Nov. 1998.
Brunet, J.F., et al., "The Inducible Cytotoxic T-Lymphocyte-Associated Gene Transcript CTLA-1 Sequence and Gene Localization to Mouse Chromosome 14," Nature 322(6076):268-271, Jul. 1986.
Bruno, A.P., et al., "Acute Myeloblastic Leukemic Cells Acquire Cellular Cytotoxicity Under Genotoxic Stress: Implication of Granzyme B and Perforin," Blood 96(5):1914-1920, Sep. 2000.
Buzza, M.S., and P.I. Bird, "Extracellular Granzymes: Current Perspectives," Biological Chemistry 387(7):827-837, Jul. 2006.
Buzza, M.S. et al., "Extracellular Matrix Remodeling by Human Granzyme B Via Cleavage of Vitronectin, Fibronectin, and Laminin," Journal of Biological Chemistry 280(25):23549-23558, Jun. 2005.
Chamberlain, C.M., and D.J. Granville, "The Role of Granzyme B in Atheromatous Diseases," Canadian Journal of Physiology and Pharmacology 85(1):89-95, Jan. 2007.

(Continued)

*Primary Examiner* — Lisa Cook
(74) *Attorney, Agent, or Firm* — Christensen O'Connor Johnson Kindness PLLC

(57) ABSTRACT

A method for identifying a subject being at risk for or having a chronic inflammatory disease, fibrillinopathy, atherosclerosis, or coronary artery disease is provided. The method may include determining the concentration of GrA and/or GrB in a blood or serum sample from said subject; and comparing the concentrations to the corresponding concentration in a control sample, wherein an elevated concentration of GrA and/or GrB may be indicative of a chronic inflammatory disease, fibrillinopathy, atherosclerosis, or coronary artery disease. The method may further include identifying concentrations of fibrinogen, elastin and/or fibrillin.

9 Claims, 14 Drawing Sheets

(56) References Cited

OTHER PUBLICATIONS

Choy, J.C., et al., "Granzyme B Induces Endothelial Cell Apoptosis and Contributes to the Development of Transplant Vascular Disease," American Journal of Transplantation 5(3):494-499, Mar. 2005.

Choy, J.C., et al., "Granzyme B Induces Smooth Muscle Cell Apoptosis in the Absence of Perforin: Involvement of Extracellular Matrix Degradation," Arteriosclerosis, Thrombosis, and Vascular Biology 24(12):2245-2250, Dec. 2004.

Choy, J.C., et al., "The Regulation and Consequences of Immune-Mediated Cell Death in Atheromatous Diseases," Cardiovascular Toxicology 3(3):269-282, Sep. 2003.

Cruz, R.P., et al., "Abstract 285: Granzymes: Major Players in Vascular Remodelling, Atherosclerosis and Longevity," Circulation 116(16)II_37, Oct. 2007.

Cruz, R.P., et al., "Granzyme B Is Expressed in Macrophage Foam Cells and Plays a Key Role in Atherosclerosis," Vascular Pharmacology 45(3):191-192, Sep. 2006.

De Boer, O.J., et al., "Epstein Barr Virus Specific T-Cells Generated From Unstable Human Atherosclerotic Lesions: Implications for Plaque Inflammation," Atherosclerosis 184(2):322-329, Feb. 2006.

Devadas, S., et al., "Granzyme B Is Critical for T Cell Receptor-Induced Cell Death of Type 2 Helper T Cells," Immunity 25(2):237-247, Aug. 2006.

Goldbach-Mansky, R., et al., "Raised Granzyme B Levels Are Associated With Erosions in Patients With Early Rheumatoid Factor Positive Rheumatoid Arthritis," Annals of the Rheumatic Diseases 64(5):715-721, May 2005.

Gordon, S., et al., "Methods for Detection of Macrophage Secretory Enzymes," in B. Bloom and J.R. David (eds.), "In Vitro Methods in Cell-Mediated and Tumor Immunity," Academic Press, New York, 1976, Chap. 27, pp. 341-352.

Hernandez-Pigeon, H., et al., "Human Keratinocytes Acquire Cellular Cytotoxicity Under UV-B Irradiation. Implication of Granzyme B and Perforin," Journal of Biological Chemistry 281(19):13525-13532, May 2006.

Hernandez-Pigeon, H., et al., "UVA Induces Granzyme B in Human Keratinocytes Through MIF: Implication in Extracellular Matrix Remodeling," Journal of Biological Chemistry 282(11):8157-8164, Mar. 2007.

Heusel, J.W., et al., "Cytotoxic Lymphocytes Require Granzyme B for the Rapid Induction of DNA Fragmentation and Apoptosis in Allogeneic Target Cells," Cell 76(6):977-987, Mar. 1994.

Hill, G.E., et al., "Aprotinin and Methylprednisolone Equally Blunt Cardiopulmonary Bypass-Induced Inflammation in Humans," Journal of Thoracic and Cardiovascular Surgery 110(6):1658-1662, Dec. 1995.

Hodge, S., et al., "Increased Airway Granzyme B and Perforin in Current and Ex-Smoking COPD Subjects," COPD 3(4):179-187, Dec. 2006.

Huang M., et al., "Detection of Apoptosis-Specific Autoantibodies Directed Against Granzyme B-Induced Cleavage Fragments of the SS-B (La) Autoantigen in Sera From Patients With Primary Sjögren's Syndrome," Clinical and Experimental Immunology 142(1):148-154, Oct. 2005.

Hunger, R.E., et al., "Detection of Perforin and Granzyme B mRNA Expressing Cells in Lichen Sclerosus," Experimental Dermatology 16(5):416-420, May 2007.

Kam, C.M., et al., "Granzymes (Lymphocyte Serine Proteases): Characterization With Natural and Synthetic Substrates and Inhibitors," Biochimica et Biophysica Acta 1477(1-2):307-323, Mar. 2000.

Kim, K.W., et al., "Human Rheumatoid Synovial Fibroblasts Promote Osteoclastogenic Activity by Activating RANKL Via TLR-2 and TLR-4 Activation," Immunology Letters 110(1):54-64, May 2007.

Kraan, M.C., et al., "T Cells, Fibroblast-Like Synoviocytes, and Granzyme B+ Cytotoxic Cells Are Associated With Joint Damage in Patients With Recent Onset Rheumatoid Arthritis," Annals of the Rheumatic Diseases 63(5):483-488, May 2004.

Mahrus, S., and C.S. Craik, "Selective Chemical Functional Probes of Granzymes A and B Reveal Granzyme B Is a Major Effector of Natural Killer Cell-Mediated Lysis of Target Cells," Chemistry & Biology 12(5):567-577, May 2005.

Poe, M., et al., "Human Cytotoxic Lymphocyte Granzyme B. Its Purification From Granules and the Characterization of Substrate and Inhibitor Specificity," Journal of Biological Chemistry 266(1):98-103, Jan. 1991.

Przybysz, M., et al., "Synovial Fibronectin Fragmentation and Domain Expressions in Relation to Rheumatoid Arthritis Progression," Rheumatology 46(7):1071-1075, Jul. 2007.

Revell, P.A., et al., "Granzyme B and the Downstream Granzymes C and/or F Are Important for Cytotoxic Lymphocyte Functions," Journal of Immunology 174(4):2124-2131, Feb. 2005.

Rosen, A., and L. Casciola-Rosen, "Altered Autoantigen Structure in Sjögren's Syndrome: Implications for the Pathogenesis of Autoimmune Tissue Damage," Critical Reviews in Oral Biology and Medicine 15(3):156-164, Jun. 2004.

Sattar, R., et al., "Bioinformatics of Granzymes: Sequence Comparison and Structural Studies on Granzyme Family by Homology Modeling," Biochemical and Biophysical Research Communications 308(4):726-735, Sep. 2003.

Sinclair, R., et al., "The Lack of Significant Changes in Scalp Hair Follicle Density With Advancing Age," British Journal of Dermatology 152(4):646-649, Apr. 2005.

Skjelland, M., et al., "Plasma Levels of Granzyme B Are Increased in Patients With Lipid-Rich Carotid Plaques as Determined by Echogenicity," Atherosclerosis 195(2):e142-e146, Dec. 2007.

Suidan, H.S., et al., "Granzyme A Released Upon Stimulation of Cytotoxic T Lymphocytes Activates the Thrombin Receptor on Neuronal Cells and Astrocytes," Proceedings of the National Academy of Sciences of the United States of America (PNAS) 91(17):8112-8116, Aug. 1994.

Sun, J., et al., "A Cytosolic Granzyme B Inhibitor Related to the Viral Apoptotic Regulator Cytokine Response Modifier A Is Present in Cytotoxic Lymphocytes," Journal of Biological Chemistry 271(44):27802-27809, Nov. 1996.

Sun, J., et al., "A New Family of 10 Murine Ovalbumin Serpins Includes Two Homologs of Proteinase Inhibitor 8 and Two Homologs of the Granzyme B Inhibitor (Proteinase Inhibitor 9)," Journal of Biological Chemistry 272(24):15434-15441, Jun. 1997.

Tak, P.P., et al., "The Levels of Soluble Granzyme A and B Are Elevated in Plasma and Synovial Fluid of Patients With Rheumatoid Arthritis (RA)," Clinical and Experimental Immunology 116(2):366-370, May 1999.

Thewissen, M., et al., "Analyses of Immunosenescent Markers in Patients With Autoimmune Disease," Clinical Immunology 123(2):209-218, May 2007.

Tremblay, G.M., et al., "Granzyme Activity in the Inflamed Lung Is Not Controlled by Endogenous Serine Proteinase Inhibitors," Journal of Immunology 165(7):3966-3969, Oct. 2000.

Tsuru, R., et al., "Increased Granzyme B Production From Peripheral Blood Mononuclear Cells in Patients With Acute Coronary Syndrome," Heart 94(3):305-310, Mar. 2008.

Vernooy, J.H., et al., "Increased Granzyme A Expression in Type II Pneumocytes of Patients With Severe Chronic Obstructive Pulmonary Disease," American Journal of Respiratory and Critical Care Medicine 175(5):464-472, Mar. 2007.

Villanueva, J., et al., "Natural Killer Cell Dysfunction Is a Distinguishing Feature of Systemic Onset Juvenile Rheumatoid Arthritis and Macrophage Activation Syndrome," Arthritis Research & Therapy 7(1):R30-R37, 2005.

Voskuyl, A.E., et al., "Levels of Circulating Cellular Fibronectin Are Increased in Patients With Rheumatoid Vasculitis," Clinical and Experimental Rheumatology 16(4):429-434, Jul.-Aug. 1998.

Wågsäter, D., et al., "Serine Protease Inhibitor A3 in Atherosclerosis and Aneurysm Disease," International Journal of Molecular Medicine 30(2):288-294, Aug. 2012.

Willoughby, C.A., et al., "Discovery of Potent, Selective Human Granzyme B Inhibitors That Inhibit CTL Mediated Apoptosis," Bioorganic & Medicinal Chemistry Letters 12(16):2197-2200, Aug. 2002.

Yawalkar, N., et al., "Perforin and Granzyme B May Contribute to Skin Inflammation in Atopic Dermatitis and Psoriasis," British Journal of Dermatology 144(6):1133-1139, Jun. 2001.

(56) References Cited

OTHER PUBLICATIONS

International Search Report mailed Nov. 28, 2008, issued in corresponding International Application No. PCT/CA2008/001752, filed Oct. 1, 2008, 4 pages.

Supplementary European Search Report mailed Sep. 6, 2010, issued in corresponding European Application No. EP 08 834 766, filed Oct. 1, 2008, 2 pages.

* cited by examiner

GRANZYME A AND GRANZYME B DIAGNOSTICS

CROSS-REFERENCES TO RELATED APPLICATIONS

This application is a division of U.S. patent application Ser. No. 12/681,349, filed Aug. 31, 2010, now U.S. Pat. No. 8,426,149, which is a National Stage of International Application No. PCT/CA2008/001752, filed Oct. 1, 2008, which claims the benefit of U.S. Provisional Application No. 60/996,139, filed Nov. 2, 2007; U.S. Provisional Application No. 60/996,138, filed Nov. 2, 2007; and U.S. Provisional Application No. 60/960,478, filed Oct. 1, 2007, each expressly incorporated herein by reference in its entirety.

TECHNICAL FIELD

This invention relates to the field of diagnostics. More particularly to the diagnosis of diseases and conditions by measuring granzyme B levels and/or granzyme A levels.

STATEMENT REGARDING SEQUENCE LISTING

The sequence listing associated with this application is provided in text format in lieu of a paper copy and is hereby incorporated by reference into the specification. The name of the text file containing the sequence listing is 41020_SEQ_Final_2013-08-12.txt. The text file is 2 KB; was created on Aug. 12, 2013; and is being submitted via EFS-Web with the filing of the specification.

BACKGROUND

The granzymes are highly conserved group of serine proteases, with five members (A, B, H, K and M) in humans and ten members (A-G, K, M-N) in mice (Sattar R. et al. Biochem Biophys Res Commun 308, 726-35 (2003). Granzyme B (GrB or cytotoxic T-lymphocyte (CTL)-associated gene transcript-1—Brunet J. F. et al. Nature 322, 268-71 (1986)), has been reported as being involved in anti-viral and anti-tumour functions, and is associated with autoimmunity, transplant rejection, graft-versus-host disease, and thymocyte development (Barry M. & Bleackley R C. Nat Rev Immunol 2, 401-9 (2002)). Granzyme A (GrA) is also involved it immune-mediated killing, and is expressed by both innate and adaptive immune cytotoxic cells.

GrB is reported to have a contribution to CTL-mediated target cell apoptosis. GrB-deficient mice possess a normal phenotype, with the exception of a slightly reduced CTL-mediated target cell apoptosis, anti-viral responses and tumour cell clearance (Revell P A. et al. J Immunol 174, 2124-31 (2005); and Heusel J W. et al. Cell 76, 977-87 (1994)), suggesting a redundancy in immune mediated cells removal. GrB-deficient recipient mice exhibit reduced allograft vasculopathy (Choy J. C. et al. Am J Transplant 5, 494-9 (2005)), and its deficiency in mice leads to increased susceptibility to allergen-induced asthma (Devadas, S. et al. Immunity 25, 237-47 (2006)).

Buzza M. S. et al. report that plasma GrA levels in normal individuals are between 15-35 pg/ml and plasma GrB levels in normal individuals are up to 15 pg/ml (Biol. Chem. 387: 827-837 (2006)). Skjelland, et al. teach that plasma levels of granzyme B are increased in patients with lipid rich carotid plaques, but also teach that normal plasma levels of GrB can be up to 100 pg/ml, while patterns with unstable plaques have plasma levels of GrB over about 100 pg/ml (and up to about 650 pg/ml) and patients with stable plaques have plasma levels of GrB between about 25 pg/ml and about 400 pg/ml (Atherosclerosis, 195:e142-e146 (2007)). Furthermore, GrB levels have been measured in the supernatant of cultured peripheral blood mononuclear cells isolated from patients at about 40 pg/ml for patients with unstable angina pectoris and at about 18 pg/ml for patients with stable angina pectoris (Tsuru R. et al. Heart 94:305-310 (2008) e-published Jun. 25, 2007). GrB has also been measured in rheumatoid arthritis patients (Goldbach-Mansky et al. Ann Rheum Dis. 64:715-721 (2005); Kraan et al. Ann Rheum Dis 63:483-488 (2004); Villanueva et al. Arthritis Res Ther 7:R30-R37 (2005)). Choy J C. et al. reported increased levels of GrB in patients with advanced atherosclerosis (Mod Pathol 16, 460-70 (2003)). GrB has also been associated with aortic aneurisms and with atherosclerosis plaque destabilization (Choy et al. Arterioscler. Thromb. Vasc. Biol.; 24; 2245-2250, (2004)). Kim et al., show that macrophages express granzyme B in the lesion areas of atherosclerosis and rheumatoid arthritis (Immunology Letters, 111, 57-65, (2007)). Increased GrB levels in Chronic Obstructive Pulmonary Disease (COPD) patients were reported in bronchoalveolar lavage (BAL) derived T-cells (Hodge et al. J. of COPD 3:179-187 (2006)). Also GrB produced protein fragments are reported in Sjögren's Syndrome patients (Huang et al. Clin Exp Immun 142:148-154 (2005)). Additionally, GrA and GrB are reported in BAL fluids from patients with inflammatory lung disease (Tremblay et al. J Immunology 165:3966-3969 (2000)). Thewissen et al. compares GrA and GrB levels in rheumatoid arthritis (RA), multiple sclerosis (MS), and between healthy individuals, and reports no change in GrA levels between healthy patients and RA or MS patients for GrA and reports a decrease in GrB levels for MS patients relative to healthy patients (Clinical Immunology 123:209-218 (2007)). GrA released in the brain may be associated with autoimmune disorders of the nervous system (Suidan et al. PNAS 91:8112-8116 (1994)). Vernooy et al. report increased GrA expression in type II pneumocytes of patients with severe COPD (Am J Respir Crit Care Med 175:464-472 (2007)). Immunodiagnostic methods for Granzymes A and B are also known (for example WO 99/54737).

SUMMARY

This invention is based, in part, on the discovery of the contribution granzyme A makes to certain diseases, including chronic inflammatory diseases, atherosclerosis or coronary artery disease, and chronic obstructive pulmonary disease (COPD), and in particular to the extracellular activity of granzyme A whereby granzyme A cleaves extracellular matrix proteins such as fibronectin.

This invention is also based, in part, on the discovery of the contribution granzyme B makes to certain diseases, including chronic inflammatory diseases, atherosclerosis or coronary artery disease, and chronic obstructive pulmonary disease (COPD), and in particular to the extracellular activity of granzyme B whereby granzyme B cleaves extracellular matrix proteins such as elastin, Fibulin-2, Fibrillin-1, and Fibrillin-2.

In one aspect of the present invention, there is provided a method for diagnosis of chronic inflammatory disease is a subject suspected of having chronic inflammatory disease or having chronic inflammatory disease, the method including: determining the concentration of GrA in a blood plasma or serum sample from the subject; and comparing the concentrations to the corresponding concentration in a control sample, wherein an elevated concentration of GrA is indicative of chronic inflammatory disease.

In a further aspect of the present invention, there is provided a method for diagnosis of atherosclerosis or coronary artery disease in a subject suspected of having atherosclerosis or coronary artery disease or having atherosclerosis or coronary artery disease, the method including: determining the concentration of GrA in a blood plasma or serum sample from the subject; and comparing the concentrations to the corresponding concentration in a control sample, wherein an elevated concentration of GrA is indicative of atherosclerosis or coronary artery disease.

In a further aspect of the present invention, there is provided a method for diagnosis of a fibrillinopathy in a subject suspected of having fibrillinopathy or having fibrillinopathy, the method including: determining the concentration of GrA in a blood plasma or serum sample from the subject; and comparing the concentrations to the corresponding concentration in a control sample, wherein an elevated concentration of GrA is indicative of fibrillinopathy.

The method may further include determining the concentration of one or more of: fibronectin; and fibrillin; with reference to the control sample as indicative of chronic inflammatory disease. The concentration of GrA, fibronectin and/or fibrillin may determined by an immunodiagnostic assay. The immunodiagnostic assay may be an enzyme-linked immunosorbent assay (ELISA), enzyme-linked immunosorbent spot (ELISPOT), dot blot, western blot, or other proteomics assay etc. The subject may have a GrA blood plasma concentration >20 pg/ml and/or a fibronectin blood plasma concentration >400 ug/ml as an indication of chronic inflammatory disease, atherosclerosis or coronary artery disease, or fibrillinopathy. The fibronectin or fibrillin, may be a fibronectin degradation product or an fibrillin degradation product. The method may further include one or more of: diagnostic imaging; clinical diagnosis and alternative laboratory diagnostics.

The chronic inflammatory disease may be selected from one or more of: rheumatoid arthritis; osteoarthritis; inflammatory bowel disease; psoriasis; hupus crythematosus; multiple sclerosis; Sjogren's syndrome; polymyositis; dermatomyositis; vasculitis; asthma and mixed connective tissue disease.

The fibrillinopathy may be selected from one or more of: Marfan syndrome; Beal's syndrome; congenital contractural arachnactyly; supravalvular aortic stenosis; Williams-Beuren syndrome; autosomal recessive cutis laxa; autosomal dominant cutis laxa; and acquired cutis laxa.

In a further aspect of the present invention, there is provided a method for diagnosis of chronic inflammatory disease in a subject suspected of having chronic inflammatory disease or having chronic inflammatory disease, the method including: determining the concentration of GrB in a blood plasma or serum sample from the subject; and comparing the concentrations to the corresponding concentration in a control sample, wherein an elevated concentration of GrB is indicative of chronic inflammatory disease.

In a further aspect of the present invention, there is provided a method for diagnosis of a fibrillinopathy in a subject suspected of having a fibrillinopathy or having a fibrillinopathy, the method including: determining the concentration of GrB in a blood plasma or serum sample from the subject; and comparing the concentrations to the corresponding concentration in a control sample, wherein an elevated concentration of GrB is indicative of fibrillinopathy.

The method may further include determining the concentration of one or more of: elastin; Fibronectin; Fibulin-2; Fibrillin-1; and Fibrillin-2; with reference to the control sample as indicative of chronic inflammatory disease. The concentration of GrB or elastin or fibrillin or fibulin or fibronectin may be determined by an immunodiagnostic assay. The immunodiagnostic assay may be an enzyme-linked Immunosorbent assay (ELISA), enzyme-linked immunosorbent spot (ELISPOT), dot blot, western blot, or other proteomics assay etc. The subject may have a GrB blood plasma concentration >40 pg/ml and/or a fibronectin blood plasma concentration >400 ug/ml as an indication of chronic inflammatory disease, or fibrillinopathy. The elastin or fibrillin or fibulin or fibronectin, may be an elastin degradation product or a fibrillin degradation product fibulin degradation product or a fibronectin degradation product. The method may further include one or more of: diagnostic imaging; clinical diagnosis and alternative laboratory diagnostics.

The chronic inflammatory disease is selected from one or more of: osteoarthritis: inflammatory bowel disease; psoriasis; lupus erythematosus: scleroderma; multiple sclerosis; polymyositis; dermatomyositis; vasculitis; asthma; and mixed connective tissue disease.

The fibrillinopathy is selected from one or more of Marfan syndrome; Beal's syndrome; congenital contractural arachnactyly; supravalvular aortic stenosis; Williams-Beuren syndrome; autosomal recessive cutis laxa; autosomal dominant cutis laxa; and acquired cutis laxa.

The chronic inflammatory disease may be arthritis. The chronic inflammatory disease may be asthma. The sample from the subject and the normal sample may be blood plasma samples or blood serum samples. The sample from the subject and the normal sample may bebronchoalveolar lavages.

A GrA concentration greater than about 20 pg/ml may be considered indicative of chronic inflammatory disease, atherosclerosis or coronary artery disease, or fibrillinopathy. A GrA concentration greater than about 21 pg/ml may be considered indicative of chronic inflammatory disease, atherosclerosis or coronary artery disease, or fibrillinopathy. A GrA concentration greater than about 22 pg/ml may be considered indicative of chronic inflammatory disease, atherosclerosis or coronary artery disease, or fibrillinopathy. A GrA concentration greater than about 23 pg/ml may be considered indicative of chronic inflammatory disease, atherosclerosis or coronary artery disease, or fibrillinopathy. A GrA concentration greater than about 24 pg/ml may be considered indicative of chronic inflammatory disease, atherosclerosis or coronary artery disease, or fibrillinopathy. A GrA concentration greater than about 25 pg/ml may be considered indicative of chronic inflammatory disease, atherosclerosis or coronary artery disease, or fibrillinopathy. A GrA concentration greater than about 30 pg/ml may be considered indicative of chronic inflammatory disease, atherosclerosis or coronary artery disease, or fibrillinopathy. A GrA concentration greater than about 35 pg/ml may be considered indicative of chronic inflammatory disease, atherosclerosis or coronary artery disease, or fibrillinopathy. A GrA concentration greater than about 40 pg/ml may be considered indicative of chronic inflammatory disease, atherosclerosis or coronary artery disease, or fibrillinopathy. A GrA concentration greater than about 45 pg/ml may be considered indicative of chronic inflammatory disease, atherosclerosis or coronary artery disease, or fibrillinopathy. A GrA concentration greater than about 50 pg/ml may be considered indicative of chronic inflammatory disease, atherosclerosis or coronary artery disease, or fibrillinopathy.

A GrB concentration greater than about 40 pg/ml may be considered indicative of chronic inflammatory disease, atherosclerosis or coronary artery disease, or fibrillinopathy. A GrB concentration greater than about 41 pg/ml may be considered indicative of chronic inflammatory disease, atherosclerosis or coronary artery disease, or fibrillinopathy. A GrB concentration greater than about 42 pg/ml may be considered indicative of chronic inflammatory disease, atherosclerosis or coronary artery disease, or fibrillinopathy. A GrB concentration greater than about 43 pg/ml may be considered indicative of chronic inflammatory disease, atherosclerosis or coronary artery disease, or fibrillinopathy. A GrB concentration greater than about 44 pg/ml may be considered indicative of chronic inflammatory disease, atherosclerosis or coronary artery disease, or fibrillinopathy. A GrB concentration greater than about 45 pg/ml may be considered indicative of chronic inflammatory disease, atherosclerosis or coronary artery disease, or fibrillinopathy. A GrB concentration greater than about 50 pg/ml may be considered indicative of chronic inflammatory disease, atherosclerosis or coronary artery disease, or fibrillinopathy. A GrB concentration greater than about 55 pg/ml may be considered indicative of chronic inflammatory disease, atherosclerosis or coronary artery disease, or fibrillinopathy. A GrB concentration greater than about 60 pg/ml may be considered indicative of chronic inflammatory disease, atherosclerosis or coronary artery disease, or fibrillinopathy. A GrB concentration greater than about 65 pg/ml may be considered indicative of chronic inflammatory disease, atherosclerosis or coronary artery disease, or fibrillinopathy. A GrB concentration greater than about 70 pg/ml may be considered indicative of chronic inflammatory disease, atherosclerosis or coronary artery disease, or fibrillinopathy. A GrB concentration greater than about 75 pg/ml may be considered indicative of chronic inflammatory disease, atherosclerosis or coronary artery disease, or fibrillinopathy. A GrB concentration greater than about 80 pg/ml may be considered indicative of chronic inflammatory disease, atherosclerosis or coronary artery disease, or fibrillinopathy. A GrB concentration greater than about 90 pg/ml may be considered indicative of chronic inflammatory disease, atherosclerosis or coronary artery disease, or fibrillinopathy. A GrB concentration greater than about 100 pg/ml may be considered indicative of chronic inflammatory disease, atherosclerosis or coronary artery disease, or fibrillinopathy.

A fibronectin blood plasma concentration >400 ug/ml may be an indication of chronic inflammatory disease, atherosclerosis or coronary artery disease, or fibrillinopathy either alone or in combination with a GrA and/or GrB concentration as set out herein. A fibronectin blood plasma concentration >450 ug/ml may be an indication of chronic inflammatory disease, atherosclerosis or coronary artery disease, or fibrillinopathy either alone or in combination with a GrA and/or GrB concentration as set out herein. A fibronectin blood plasma concentration >500 ug/ml may be an indication of chronic inflammatory disease, atherosclerosis or coronary artery disease, or fibrillinopathy either alone or in combination with a GrA and/or GrB concentration as set out herein. Furthermore, concentrations of elastin, Fibulin-2, Fibrillin-1, and/or Fibrillin-2 or degradation products thereof may be indicative of chronic inflammatory disease, atherosclerosis or coronary artery disease, or fibrillinopathy in a subject. Alternatively, the methods described herein may also be used to make a diagnosis of COPD in a subject.

In a further aspect of the present invention, there are provided kits, commercial packages and uses for the diagnosis of chronic inflammatory disease, atherosclerosis or coronary artery disease, or fibrillinopathy. The kits and commercial packages may also include one or more of: reagents, antibodies, normal controls, a listing of normal levels and those associated with a diagnosis of one or more of chronic inflammatory disease, atherosclerosis or coronary artery disease, or fibrillinopathy or COPD, and/or instructions for their use. The methods may also be used in conjunction with know diagnostic methods.

DETAILED DESCRIPTION

Figure 1:
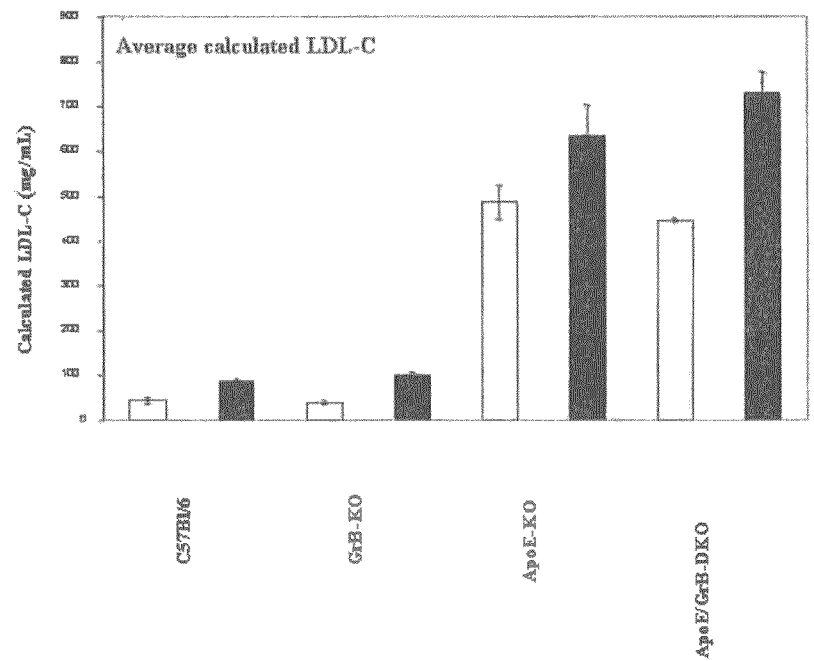
FIG. 1 is a bar graph showing the average calculated LDL-C in the plasma of C57/Bl/6, GrB KO, ApoE KO or ApoE/GrB DKO mice. White bars represent mice fed a normal chow diet; black bars represent mice fed a Western diet. N=3 for each group. Calculated LDL-C (mg/ml) is the Y-axis.

The methods described herein for identifying a subject being at risk for or having one or more of: a chronic inflammatory disease; fibrillinopathy; atherosclerosis; or coronary artery disease; may be practiced alone or in combination depending on the result desired and the subject being tested. The method may include determining the concentration and/or relative amount of GrA and/or GrB in a blood or serum sample from the subject; and comparing the concentration and/or relative amount to the corresponding concentration in a control sample, wherein an elevated concentration and/or relative amount of GrA and/or GrB may be indicative of a chronic inflammatory disease, fibrillinopathy, atherosclerosis, or coronary artery disease. The method may further include identifying a concentration and/or relative amount of one or more of fibrinogen, elastin and/or fibrillin. Where the concentration and/or relative amount of GrA is determined it may also be informative to know the concentration and/or relative amount of one or more of fibrinogen and/or fibrillin. Where the concentration and/or relative amount of GrB is determined it may also be informative to know the concentration and/or relative amount of one or more of elastin and/or fibrillin. A control sample may be obtained from one or more control subjects. Control subjects do not having any one or more of a chronic inflammatory disease; fibrillinopathy; atherosclerosis; or coronary artery disease.

When the concentration and/or relative amount of GrA is determined, the chronic inflammatory disease may be selected from one or more of rheumatoid arthritis; osteoarthritis; inflammatory bowel disease; psoriasis; lupus erythematosus; multiple sclerosis; Sjogren's syndrome; polymyositis; dermatomyositis; vasculitis; asthma and mixed connective tissue disease. When the concentration and/or relative amount of GrA is determined, the fibrillinopathy may be selected from one or more of: Marfan syndrome; Beal's syndrome; congenital contractural arachnactyly; supravalvular aortic stenosis; Williams-Beuren syndrome; autosomal recessive cutis laxa; autosomal dominant cutis laxa; and acquired cutis laxa.

When the concentration and/or relative amount of GrB is determined the chronic inflammatory disease may be selected from one or more of: selected from one or more of: osteoarthritis; inflammatory bowel disease; psoriasis; lupus erythematosus; scleroderma; multiple sclerosis; polymyositis; dermatomyositis; vasculitis; asthma; and mixed connective tissue disease. When the concentration and/or relative amount of GrB is determined, the fibrillinopathy may be selected from one or more of: selected from one or more of Marfan syndrome; Beal's syndrome; congenital contractural arachnactyly; supravalvular aortic stenosis; Williams-Beuren syndrome; autosomal recessive cutis laxa; autosomal dominant cutis laxa; and acquired cutis laxa.

The fibronectin or fibrillin, may be a fibronectin degradation product or an fibrillin degradation product. The elastin or fibrillin, may be an elastin degradation product or a fibrillin degradation product.

The method may, for example, further include one or more of: diagnostic imaging; clinical diagnosis and alternative laboratory diagnostics. Diagnostic imaging may be selected from one or more of X-ray, computed tomography (CT) scanning, angiography, magnetic resonance imaging; (MRI), ultrasound (for example, see echogenicity vessel plaque assessment in Skjelland, et al. Atherosclerosis, 195:e142-e146 (2007)), depending on the disease indication and as known in the art. Clinical diagnosis may depend on the disease indication and is well within the skill and knowledge of a person of skill in the art. Alternative laboratory diagnostics may be selected from any number of known assay methods, but excluding determining the concentration and/or relative amount of GrA and/or GrB in a blood or serum sample from a subject and comparing the concentration and/or relative amount to the corresponding concentration in a control sample, and/or may further exclude Identifying one or more concentrations and/or relative amounts of one or more of fibrinogen, elastin and/or fibrillin.

"Atherosclerosis" (or "Arteriosclerosis") in the present context are potential; causes of coronary artery disease. Atherosclerosis is a built up of plaque on the inside of arteries. Atherosclerosis is characterized by the thickening of the arterial wall, usually at sites in the arterial tree where laminar flow is disrupted. This inflammatory vasculopathy is characterized by the excessive accumulation of lipids and modified lipids is the intima, medial damage, and the thickening and structural re-organization of the vessel wall. Physical forces, or the exposure to elevated levels of circulating low density lipoprotein (LDL) or free radicals caused by smoking, hypertension, or diabetes mellitus can cause endothelial dysfunction. These factors alter endothelial function by increasing the release of pro-inflammatory cytokines and vasoactive substances, which can result in interference with normal antithrombotic properties and permeable barrier functions, and increasing expression of cell-surface adhesion molecules. Atherosclerosis begins as a fatty streak consisting of atherogenic lipoproteins entering the intima and becoming modified. The increase of cell-surface adhesion molecules causes the recruitment and intravasation of leukocytes, monocytes and T-cells. Pro-inflammatory cytokines expressed within the developing lesion provide chemotactic stimulus to the adherent leukocytes, increasing their migration into the intima. Monocyte colony stimulating factor (M-CSF), which is also produced in the plaque, augments the expression of macrophage scavenger receptors to uptake modified lipids. Macrophages phagocytose this modified lipid in an unregulated manner, causing the formation of foam cells, which make up the fatty streak. Leukocytes, as well as resident vascular wall cells, secrete cytokines and growth factors that promote the migration and proliferation of smooth muscle cells (SMC). Vascular SMC (VSMC) may also release factors that degrade elastin and collagen in response to inflammatory stimulation, which allows the cells to migrate through the elastic lamina and collagenous matrix. VSMC proliferate and migrate from the media to the developing plaque in the intima, and contribute to the fatty streak development into an intermediate lesion by excessive extracellular matrix (ECM) secretion. This ECM increases the retention and aggregation of lipoproteins. As the plaque continues to grow, additional lymphocyte recruitment follows, and VSMC form a fibrotic cap under the endothelial layer. The fibrous cap eventually becomes thin and weak by a combination of an inhibition of collagen synthesis from VSMC and the expression of collagenases by foam cells. Eventually, a lesion can develop that is vulnerable to rupture, exposing thrombogenic material in the form of necrotic foam cells. The plaque may also grow without rupture, and may eventually obstruct blood flow. The formation of a thrombus which may block blood flow or the obstruction of a vessel from plaque formation can lead to ischemia of distal tissue.

"Fibrillinopathies" (type 1) are caused by defects in the fibrillin-1 protein (from FBN1gene). While Marfan syndrome is the most common type of fibrillinopathy, not all mutations in the FBN1 gene cause this syndrome. FBN1 mutations cause a spectrum of connective tissue disorders, with a broad range is severity and age of onset. Some FBN1 mutations cause a severe disorder that is fatal to newborns, while other mutations cause adult onset fibrillinopathies with a single abnormality, such as a dislocated lens in the eye or an abnormal aorta.

"Marfan syndrome" (or Marfan's syndrome) is a genetic disorder of the connective Tissue. It is sometimes an inherited dominant trait (carried by the FBN1 gene). The FBN1 gene encodes a connective protein called fibrillin-1. The most serious complication is defects of the heart valves and aorta. It may also affect the lungs, eyes, dural sac surrounding the spinal cord, skeleton and hard palate.

"Beals syndrome" (or Arachnodactyly, Coutractural Beals Type, Beals-Hecht Syndrome, Congenital Contractural Arachnodactyly (CCA)) is an extremely rare genetic disorder caused by a mutation in fibrillin-2 gene (FBN2) and characterized by the permanent fixation of certain joints (e.g., fingers, elbows, knees, and hips) in a flexed position (contractures); abnormally long, slender fingers and toes (arachnodactyly); permanently flexed fingers (camptodactyly); and/or abnormally shaped ears resulting in a "crumpled" appearance. In addition, affected individuals may exhibit front-to-back and side-to-side curvature of the spine (kyphoscoliosis); feet that are abnormally positioned (talipes equinovarus or clubfoot); outward displacement of the fingers (ulnar deviation of the fingers); an abnormally short neck; and/or displacement of the lens of the eye (ectopia lentis). In some cases, affected individuals may have a slight deformity of the valve on the left side of the heart (mitral valve prolapse). Beals syndrome is inherited as an autosomal dominant trait.

"Supravalvular aortic stenosis" (or SVAS) is a fixed form of congenital left ventricular outflow tract (LVOT) obstruction that occurs as a localized or a diffuse narrowing of the ascending aorta beyond the superior margin of the sinuses of Valsalva. It accounts for less than 7% of all fixed forms of congenital LVOT obstructive lessons. SVAS may occur sporadically, as a manifestation of elastin arteriopathy, or as part of Williams syndrome.

"Williams syndrome" (or WS, Williams-Beuren syndrome, WBS) is a rare neurodevelopmental disorder caused by a deletion of about 26 genes from the long arm of chromosome 7. It is characterized by a distinctive, "elfin" facial appearance, along with a low nasal bridge; an unusually cheerful demeanor and case with strangers, coupled with unpredictably occurring negative outbursts; a predisposition to violent outbursts; mental retardation coupled with unusual (for persons who are diagnosed as mentally retarded) language skills; a love for music; and cardiovascular problems, suck as supravalvular aortic stenosis and transient hypercalcaemia. The deleted region typically includes CLIP2, ELN, GTF2I, GTF2IRD1, and LIMK1. Loss of the ELN gene (elastin), is associated with the connective-tissue abnormalities and cardiovascular disease (specifically supravalvular aortic stenosis (SVAS) and supravalvular pulmonary stenosis (SVPS)) found in many people with this syndrome.

"Cutis laxa" (or CL) is a rare, inherited or acquired connective tissue disorder in which the skin becomes inelastic and hangs loosely in folds. The clinical presentation and the mode of inheritance show considerable heterogeneity. Autosomal dominant, autosomal recessive, and X-linked recessive patterns have been noted in inherited forms. A serine to proline amino acid substitution in the fibulin 5 (FBLN5) gene has been associated with abnormal elastogenesis, resulting in a recessive form of CL in humans. The X-linked form is currently classified in the group of copper transport diseases. The precise cause is unknown, but it may be due to abnormal elastin metabolism resulting in markedly reduced dermal elastin content.

Methods for identifying a subject being at risk or having a chronic inflammatory disease, fibrillinopathy atherosclerosis, and/or coronary artery disease, may be supplemented by, in addition to identifying a level of granzyme A or B in a first sample from the subject, identifying a level of fibronectin or a level of elastin or a level of fibrillin in a second sample from the subject, identifying a level fibronectin or a level of elastin or a level of fibrillin in a second normal sample from the normal subject not at risk or having the a chronic inflammatory disease, fibrillinopathy, atherosclerosis, and/or coronary artery disease and comparing the level of granzyme A or B in the first sample from the subject to the level of granzyme B in the first normal sample from the normal subject as well as comparing the level of fibronectin or elastin or fibrillin in the second sample from the subject to the level of fibronectin or elastin or fibrillin in the second normal sample from the normal subject. The subject is more likely to be at risk for or having a chronic inflammatory disease, fibrillinopathy, atherosclerosis, and/or coronary artery disease when the level of fibronectin or elastin or fibrillin in the second sample from the subject is lower than the level of fibronectin or elastin or fibrillin in the second normal sample from the normal subject or the level of fibronectin or elastin or fibrillin fragments are higher in the blood than normal subjects. Granzyme A or B cleaves extracellular matrix proteins and when a subject has an elevated or high level of granzyme A or B as described above, the level of extracellular matrix proteins in the subject will be reduced by the action of granzyme A or B and increased fragments may appear in the blood. The longer that high levels of granzyme A or B have been active, the lower the tissue levels of extracellular matrix proteins will be at the disease sites. Baseline levels in healthy subjects for GrB is <40 pg/ml and for GrA is <20 pg/ml. Similarly, about 325 ug/ml of fibronectin in the blood is a good baseline in healthy subjects (Stathakis et al., J. Clin. Pathol. 34:504-508 (1981)).

Antibody Production

One methodology is to detect the presence of GrA or GrB or elastin or fibronectin or fibrillin specific peptides or proteins. GrA or GrB or elastin or fibronectin or fibrillin specific peptides or proteins may also include degradation products thereof. These peptides or proteins may be detected by isolating proteinaceous material from a biological sample and determining the sequence of peptides or proteins so isolated and comparing to the known sequence of GrA or GrB or elastin or fibronectin or fibrillin proteins. Preferably, such detecting will make use of an intermediate agent such as an antibody specific for the GrA or GrB or elastin or fibronectin or fibrillin peptide or protein as known in the art.

Antibodies to GrA or GrB or elastin or fibronectin or fibrillin peptides or proteins may be prepared by a variety of known methods. Such antibodies may be polyclonal, monoclonal, or may be fragments of antibodies.

For the production of antibodies, various hosts including goats, rabbits, rats, mice, humans, and others, may be immunized by injection with a GrA or GrB or elastin or fibronectin or fibrillin peptide or protein fragment which has immunogenic properties. Depending on the host species, various adjuvants may be used to increase immunological response. Such adjuvants include, but are not limited to, Freund's, mineral gels such as aluminum hydroxide, and surface active X substances such as lysolecithin, pluronic polyois, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that GrA or GrB or elastin or fibronectin or fibrillin or fibrillin peptides, fragments, or oligopeptides used to induce antibodies have an amino acid sequence consisting of at least five amino acids, and more preferably at least 10 amino acids. It is also preferable that they are identical to a portion of the amino acid sequence of the natural protein, and they may contain the entire amino acid sequence of the GrA or GrB or elastin or fibronectin or fibrillin peptide or protein. Short stretches of GrA or GrB or elastin or fibronectin or fibrillin amino acids may be fused with those of another protein such as keyhole limpet hemocyanin and antibody produced against the chimeric molecule.

Peptides corresponding to a GrA or GrB or elastin or fibronectin or fibrillin amino acid sequence may be synthesized using methods known in the art, including the recombinant techniques disclosed in the examples below. Such peptides may also be made to incorporate a N-terminal cysteine to facilitate conjugation to other molecules (e.g. to enhance Immunogenicity) with such conjugation being mediated by an agent such as m-maleimidobenzoyl-N-hydroxysuccinimide ester (MBS). Antibodies that specifically react with the peptide may be purified from the antisera by affinity chromatography for example by using Cellulofine (Seikagaku Corporation) conjugated with the peptide. The resulting antibodies may be tested by immunoblotting.

Monoclonal antibodies to GrA or GrB or elastin or fibronectin or fibrillin peptides or proteins or anti-idiotypic monoclonal antibodies may be prepared using any technique, which provide for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell Biol. 62:109-120).

One process for obtaining the hybridomas of this invention involves starting from spleen cells of an animal, e.g. mouse or rat, previously immunized in vivo or from spleen cells of such animate previously immunized in vitro with an antigen and fusing the immunized cells with myeloma cells under hybridoma-forming conditions; and selecting those hybridomas which secrete the monoclonal antibodies which are capable of specifically recognizing the GrA or GrB or elastin or fibronectin or fibrillin peptide or protein.

Selected hybridomas are cultured in appropriate culture medium; and then the secreted monoclonal antibodies are recovered; or alternatively the selected hybridoma is implanted into the peritoneum of a mouse and, when ascites has been produced in the animal; the monoclonal antibodies formed from the ascites are recovered. Monoclonal antibodies of the invention may be prepared by conventional in vitro techniques such as the culturing of immobilized cells using e.g. hollow fibers or microcapsules or such as the culturing of cells in homogeneous suspension using e.g. airlift reactors or stirred bioreactors.

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce GrA or GrB or elastin or fibronectin or fibrillin-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120-3). Such single chain antibodies may also be used for production anti-idiotypic antibodies for use in this invention.

Antibodies may also be produced by inducing in vivo production in the lymphocyte population or by screening recombinant immunoglobulin libraries or panels of highly specific binding reagents as disclosed in the literature (Orlandi, R, et al. (1989) Proc. Natl. Acad. Sci. 86:3833-3837; Winter, G. et al. (1991) Nature 349:293-299).

Antibody fragments which contain specific binding sites specific for GrA or GrB or elastin or fibronectin or fibrillin peptides or proteins or for anti-GrA or GrB or elastin or fibronectin or fibrillin antibodies may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively Fab expression libraries may be constructed to allow rapid and easy identification of monoclonal Fab fragments with the desired specificity (Huse, W. D. et al. (1989) Science 254:1275-1281). Such fragments when specific for anti-GrA or GrB or elastin or fibronectin or fibrillin antibodies may be used for production of anti-idiotypic antibodies or fragments thereof.

Monoclonal antibodies of this invention may be "chimeric", an example of which is an animal antigen-binding variable domain coupled to a human constant domain (Cabilly et al., U.S. Pat. No. 4,856.567; Morrison, S. L. et al., Proc. Natl. Acad. Sci. USA 81:6851-6855 (1984); Boulianne, G. L. et al. Nature 312:643-646 (1984); Neuberger, M. S. et al. Nature 314:268-270 (1985)). The term "chimeric" antibody describes a polypeptide comprising at least the antigen binding portion of an antibody molecule linked to at least part of another protein such as an immunoglobulin constant domain. However, antibodies of this invention may be conjugated to a variety of moieties including labeling moieties.

Various immunoassays may be used for screening to identify antibodies having a desired specificity. Numerous protocols for competitive binding or immunoradiometric assays using either polyclonal or monoclonal antibodies with established specificities are well known in the art. Such immunoassays typically involve the measurement of complex formation between a GrA or GrB or elastin or fibronectin or fibrillin antigen and its specific antibody Monoclonal-based immunoassays utilizing monoclonal antibodies reactive to at least two non-interfering epitopes are preferred, but competitive binding assays may also be employed (Maddox, D. E. et al. (1983; J. Exp. Med. 158:1211-1216).

Antibody Assay Methods

One of the most important utilities of the antibodies and proteins/peptides of the invention is for diagnostic purposes, in particular in assays to detect of quantify the presence of GrA or GrB or elastin or fibronectin or fibrillin antibodies or antigen (GrA or GrB or elastin or fibronectin or fibrillin protein or peptide) in a sample. In the following, such assays, in particular ELISAS (enzyme-linked immunosorbent assays) and Western blots can be used to detect GrA or GrB or elastin or fibronectin or fibrillin proteins or peptides in samples. Numerous immunoassays are known in the art (Methods in Cell Biology, Vol. 37: Antibodies in Cell Biology Asai, ed., Academic Press, Inc., New York. (1993); and Basic and Clinical Immunology, 7$^{th}$ ed., Stites & Terr, eds., (1991)).

A preferred method for detecting GrA or GrB or elastin or fibronectin or fibrillin proteins is the ELISA, in which an antibody typically is bound to an enzyme, such as peroxidase or phosphatase, which can produce colored reaction products from an appropriate buffer. Thus, it utilizes a tagged antigen molecule of known quantity to determine an unlabelled antigen of unknown quantity. Preferably, a GrA or GrB or elastin or fibronectin or fibrillin protein according to the invention, or a suitable functional fragment thereof, is used coupled to a conventional tag, such as His6.

Thus, in an ELISA format according to the invention, polypeptides or proteins specific for GrA or GrB or elastin or fibronectin or fibrillin are detected and/or quantified, preferably in a biological sample. The sample may be any sample of biological tissue or fluid, suck as blood. The sample is pretreated as necessary by dilution in a suitable buffer solution or concentrated, if desired. Any number of standard aqueous buffer solutions may be used, such as Tris or the like, at physiological pH. Samples are incubated with an excess of the protein according to the invention as antigen. After rinsing to remove any unbound antigen, the amount of bound antigen is quantitated by adding a solution of enzyme-conjugated antibody that binds to constant domains of antibodies in the sample. Excess conjugated antibody is rinsed away and the activity of the bound enzyme is determined by adding the substrate to the reaction and measuring the formation of products. As the products of the reactions used in ELISA procedures are colored, the amount of product formed can readily be determined by the intensity of the colour that has developed using a spectrophotometer. The activity of the bound enzyme is proportional to the amount of antigen-binding antibody in the sample; therefore, the original concentration of such antibodies can be estimated from a series of control assays employing known concentrations of specific antigens. Similarly, antibodies to GrA or GrB or elastin or fibronectin or fibrillin can be detected in a biological sample using bound antigen (GrA or GrB or elastin or fibronectin or fibrillin protein or peptide).

As an alternative method for detecting GrA or GrB or elastin or fibronectin or fibrillin proteins western blots can be utilized taking advantage of the GrA or GrB or elastin or fibronectin or fibrillin specific antibodies described above. Biologic samples containing proteins can be assayed by fractionation on polyacrylamide gels under denaturing conditions. Alternatively, tris tricine polyacrylamide gel electrophoresis can be used for improved separation of small peptides in the range from 1 to 100 kDa (Schägger H. and von Jagow G. ((1987) Analytical Biochemistry 166:368-379 and Klafki H.-W. et al. (1996) Analytical Biochemistry 237, 24-29.). The proteins seperated in the gels can then be transferred to a membrane using a variety of methods known in the art. Membranes can then be probed using GrA or GrB or elastin or fibronectin or fibrillin specific antibodies in a western blot to identity the proteins of interest in the biological sample preparations. Numerous Western blotting methods are known in the art (ECL western blotting protocol—Amersham; Hsu SM. Methods Enzymol (1990)184:357-63; Leong M M. and Fox G R. Methods Enzymol (1990) 184:442-51). Immunodiagnostic method for granzymes A and B are also described in WO 99/54737.

Western Blotting

As an alternative method for detecting GrA or GrB or elastin or fibronectin or fibrillin proteins or peptides western blots can be utilized taking advantage of the GrA or GrB or elastin or fibronectin or fibrillin specific antibodies described above. Biologic samples containing proteins can be assayed by fractionation on polyacrylamide gels under denaturing conditions. Alternatively, tris tricine polyacrylamide gel electrophoresis can be used for improved separation of small peptides in the range from 1 to 100 kDa (Schägger H. and von Jagow G. (1987) Analytical Biochemistry 166:368-379 and Klafki H.-W. et al. (1996) Analytical Biochemistry 237, 24-29.). The proteins separated in the gels can then be transferred to a membrane using a variety of methods known in the art. Membranes can then be probed using GrA or GrB or elastin or fibronectin or fibrillin specific antibodies in a western blot to identify the proteins or peptides or degradation products thereof of interest in the biological sample preparations. Numerous Western blotting methods are known in the art (ECL western blotting protocol—Amersham; Hsu S M. Methods Enzymol (1990) 184:357-63; Leong M M, and Fox G R. Methods Enzymol (1990) 184:442-51).

Alternatively GrA or GrB enzyme-linked immunosorbent spot (ELISPOT—Czerkinsky C. et al. (1983) J Immunol Methods 65 (1-2): 109-21), dot blots or other proteomic approaches known in the art.

Various alternative embodiments and examples of the invention are described herein. These embodiments and examples are illustrative and should not be construed as limiting the scope of the invention.

EXAMPLES

Methods and Materials

Mice

All animal protocols were approved by the University of British Columbia (UBC) Animal Care Committee. C57Bl/6 mice, C57Bl/6-ApoE−/− and C57Bl/6-GrB−/− mice were obtained from Jackson Laboratories™ (Bar Harbor, Me.) (PIEDRAHITA et al. 1992. *Proc Natl. Acad Sci* 89: 4471-4475; HEUSEL et at 1994 *Cell* 76:977-987). The C57Bl/6-ApoE−/− x GrB−/− double knockout (ApoE/GrB-DKO) mice were generated by crossing the C57Bl/6-ApoE−/− and C57Bl/6-GrB−/− mouse strains. Genotyping of the mice was performed using primers and PCR reactions designed for genotyping these lines from Jackson Laboratories™ (GrB primers: 5'-TGAAG ATCCT CCTGC TACTG C-3' (SEQ ID NO: 1) and 5'-TCCTG AGAAA GACCT CTGCC-3' (SEQ ID NO: 2); ApoE primers: 5'-GCCTA GCCGA GGGAG AGCCG-3' (SEQ ID NO: 3) and 5'-TGTGA CTTGG GAGCT CTGCA GC-3' (SEQ ID NO: 4)). The pups were weaned at 3 weeks of age and then maintained on a 12-hour day and night cycle with food and water provided ad libitum. At 6-8 weeks of age, mice were maintained on either regular chow or a Western high fat diet (Harlan Teklad™) for 30 weeks and were sacrificed to collect blood and tissues.

Tissue and Blood Collection

Animals were overdosed with 2.5% Avertin™ (Sigma™) and perfusion fixed with four mL of 4% formalin (Sigma™)

at a flow rate of 2 mL/min. The hearts were then rapidly removed, and aortic root sections were OCT-embedded. Skin samples taken from the back were either OCT-embedded (Tissue-Tek™) or immersion-fixed in 10% formalin for 24 h before being embedded in paraffin. Blood extracted by cardiac puncture was collected in EDTA microvette tubes (Sarstedt™), spun at 10,000×g for 7 minutes at 4° C., and the separated serum stored at −80° C. until required for analysis.

Hair Removal

The animal was deeply anesthetized with 2.5% avertin (Sigma) and fur as removed with 10 ml of chemical hair remover (NAIR™, Church and Dwight Co.) distributed evenly with a swab. After 15 minutes of incubating, the NAIR™ and fur was removed with warm water and dried with paper tissues.

Immunofluorescence

Immunofluorescence was performed on OCT-embedded frozen sections. Briefly, sections were fixed with acetone for 10 min. Background staining was blocked by incubation of sections with Dako™ protein block (Dako Cytomation™) for 20 minutes then incubation in 10% donkey serum for 1 hour. Sections were incubated in goat anti-granzyme B (Santa Cruz™, 1:50) and rat anti-mouse macrophage/monocyte (Chemicon, 1:50) at 4° C. overnight, followed by incubation in donkey anti-goat IgG (Alexa Fluor™ 594, 1:500) and donkey anti-rat IgG (Alexa Fluor™ 488, 1:500) for 30 min at room temperature in the dark. Slides were mounted with VECTASHIELD™ Hard-set mounting medium with DAPI (Vector Laboratories™, Burlingame, Calif.). Confocal microscopy wax performed using a Leica AOBS™ SP2 confocal microscope.

Histological Assessment and Quantitation

Serial 10 µm sections of the aortic roots isolated as described stained with hematoxylin & eosin, Movat's pentachrome, elastic van Gieson or Oil Red O. ImageProPlus™ (MediaCybernetics™, Silver Spring. Md.) was used to quantify the lesion area per cross section in ten to twenty sections per mouse which were dress averaged to provide mean lesion area per mouse.

Statistics

An ANOVA test was performed to determine statistical differences between multiple groups. Statistical differences between two groups were determined using a Student's t-test. For both tests, a p value (alpha error) of 0.05 or less was considered significant.

Example 1

ApoE/Granzyme B Double Knock-Out Mice

Figure 4:
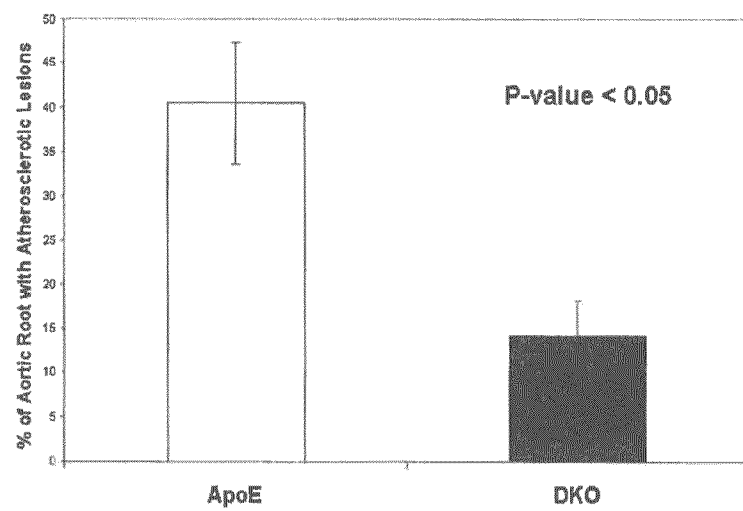
FIG. 4 shows the percentage area of the aortic root in ApoE KO (white bar) and ApoE/GrB DKO (black bar) mice fed a Western diet. N=2 for the DKO mice, N=4 for the ApoE KO mice. Values for each section was calculated (sum of the plaque area)/(total aortic root area)*100%. For each animal, 3-7 sections of aortic roots were analyzed for % lesion area and averaged.
Figure 5:
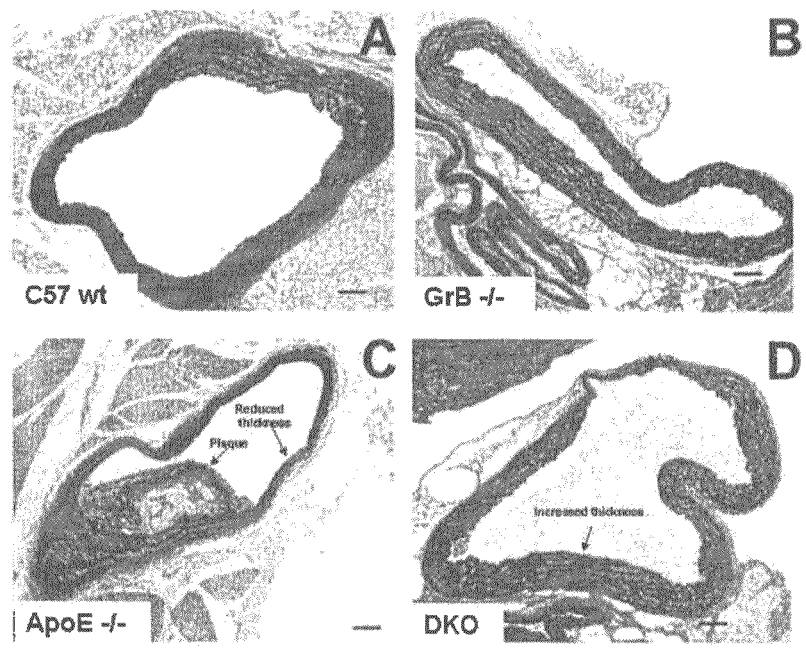
FIG. 5 Representative artery sections from mice fed a Western diet for 30 weeks. (A)C57 WT, (B) GrB-/-, (C) ApoE-/-, (D) ApoE/GrB-DKO.

Four groups of mice consisting of (1) C57Bl/6 wild-type, (2) C57/ApoE−/− (ApoE-KO). (3) C57/GrB−/− (GrB-KO), and (4) C57 GrB/ApoE-DKO were fed a normal chow or high fat 'Western' diet (21% fat, 0.2% cholesterol) for 30 weeks. No obvious phenotypic differences were observed in these mice during the first 3 months. Mice were sacrificed and tissues harvested at 30 weeks of age (ApoE KO mice on the Western diet are sacrificed around this age for humane reasons). As reported in the literature, the ApoE-KO mice had developed severe skin xanthomatosis, hair loss, hair discoloration and numerous atherosclerotic lesions. Surprisingly, the GrB/ApoE-DKO mice demonstrated a significant reduction in both frequency and size of atherosclerotic lesions (FIG. 4). Atherosclerotic lesions in the ApoE/GrB DKO mice decreased in size to less than 15% of the aortic root area, from more than 40% in the ApoE KO mice fed a Western diet.

Figure 2:
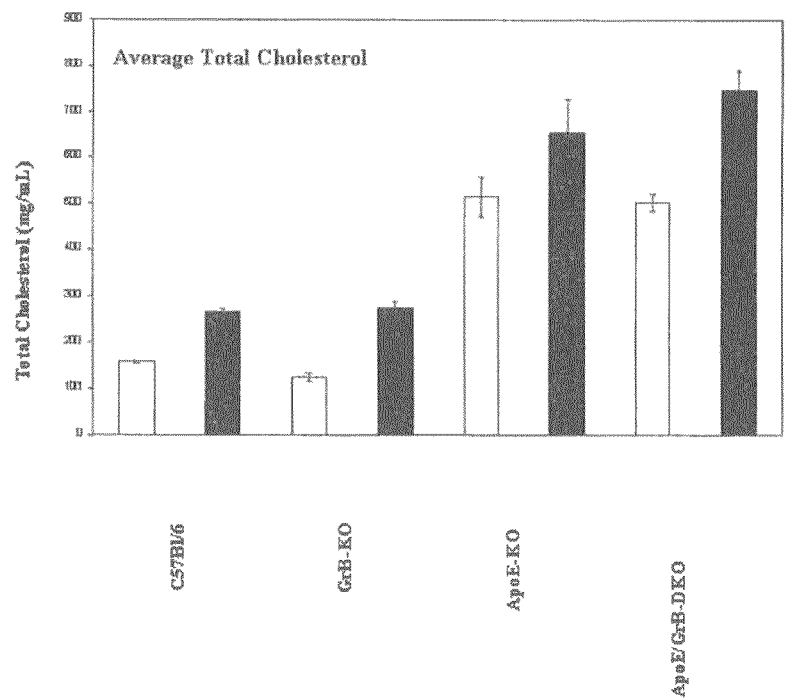
FIG. 2 is a bar graph showing the average total cholesterol in the plasma of C57/Bl/6, GrB KO, ApoE KO or ApoE/GrB DKO mice. White bars represent mice fed a normal chow diet; black bars represent mice fed a Western diet. N=3 for each group. Total cholesterol (mg/ml) is the Y-axis.
Figure 3:
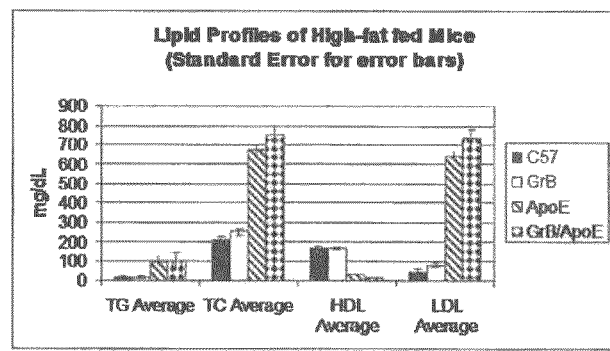
FIG. 3 is a bar graph showing the plasma lipid profiles of C57/Bl/6 (solid bar), GrB KO (white bar), ApoE KO (hatched bar) or ApoE/GrB DKO (checked bar) mice on a Western diet. TG average—average triglycerides: TC average—total cholesterol average. N=3 for each group.

Interestingly, this difference in atherosclerotic lesions is not due to a change in blood cholesterol or lipoprotein levels, as there is no difference between the ApoE KO and the ApoE/GrB DKO mice (FIGS. 1 & 2)—both total cholesterol and LDL-C plasma concentrations are the same. No significant differences in HDL, LDL and triglycerides are observed between ApoE KO (hatched bars) and ApoE/GrB DKO (checked bars) mice fed a Western diet (FIG. 3). Removal of granzyme B activity alone (white bars) does not have a significant effect on the blood lipid profiles compared to the C57/BL6 (black bar).

At 30 weeks, the DKO mice had no visible xanthomas (Table 1). The DKO mice have smooth and unwrinkled skin. The difference in the incidence of xanthomatosis was surprising, as no previous link between granzyme B and xanthomatosis had been previously identified.

TABLE 1

Cutaneous xanthomatosis is abolished in the absence of granzyme B activity.

| Genotype | Xanthomatosis present |
|---|---|
| C57 | 0/8 mice |
| GrB-KO | 0/10 mice |
| ApoE-KO | 9/11 mice |
| ApoE/GrB DKO | 0/9 mice |

The fur in the ApoE mice is patchy, discoloured (graying) and held weakly in the skin (easily removed by depilatory), while surprisingly, the ApoE/GrB DKO mice retain their dark fur and does not discolour, and is held firmly in the skin—even more so than the granzyme B KO mice. The hair follicles in the GrB KO and the ApoE/GrB DKO mice are more abundant and embedded deeper in the fatty layer of the skin, compared to the wild-type or the ApoE KO mice (Table 2). A standard Nair-mediated hair removal procedure takes more than 45 minutes in the GrB KO and ApoE/GrB DKO mice, compared to 5 minutes in the wild-type or ApoE KO mice.

TABLE 2

Hair follicle density and distribution - Values indicate number of follicles per ~8.9 mm$^2$. N = 2 for each strain

| Mouse Strain | Epidemis and Dermis | Sub-dermis |
|---|---|---|
| C57/Bl6 | 12 | 10 |
| GrB KO | 25 | 6 |
| ApoE KO | 12 | 2 |
| ApoE/GrB DKO | 40 | 36 |

ApoE KO mice exhibit signs of premature aging, necessitating sacrifice by about 30 weeks (6-7 months) of age, however the ApoE/GrB DKO mice remain healthy and vigorous beyond 12 months of age, with no visible signs of aging or illness. This was surprising, as no support or indication of a role for GrB in longevity has been previously identified in the literature.

Co-localization of granzyme B and macrophages in the lesions of the aortic roots were performed and imaged by confocal microscopy. The ApoE−/− lesions showed both granzyme B and macrophage staining, however co-localization of both occurred at specific regions of the plaque: the fibrotic cap and the shoulder regions. Granzyme B staining was localized at the internal elastic lamina.

Example 2

Elastin and Granzyme B Distribution in Aortic Sections

Colocalization of granzyme B and macrophages in the lesions of the aortic roots were performed and imaged by confocal microscopy. The lesion of the ApoE-KO mice showed both granzyme B and macrophage staining, however colocalization of both occurred at specific regions of the plaque: the fibrotic cap and the shoulder regions. Granzyme B staining was localized to the elastic lamellae.

In order to adhere to the aortic walls, smooth muscle cells require elastin. Aortas of C57 wt, GrB-/-, ApoE-/- and DKO mice were stained with elastic van Gieson (FIG. 5A to 5D). The aortic wall of the ApoE mouse is very thin and elastin staining is markedly reduced compared to the C57 wt. In the DKO mouse, the aorta wall is significantly thicker and elastin staining is correspondingly more intense. GrB also colocalizes with the internal elastic lamina of atherosclerotic plaques and an influx of macrophages in the ApoE-/-. Surprisingly, this colocalization is not observed in the DKO mice, as demonstrated by confocal microscopy staining.

The increased localization of granzyme B with the internal elastic lamina indicates that it may accumulate on elastin fibres and over time, contribute to degradation of elastin. This in turn would lead to reduced elasticity, production of fragments that enhance inflammation, increased calcification and overall stiffness (hardening) of blood vessels. Reduced elastin in the internal elastic lamina also promotes migration of smooth muscle cells in to the intima (intimal hyperplasia) and the formation of atherosclerotic plaques. The fragmented and degraded elastin (by granzyme B) may lead to recruitment of immune cells of the lesion.

Example 3

Reduced Cutaneous Inflammation in DKO Mice

Figure 6:
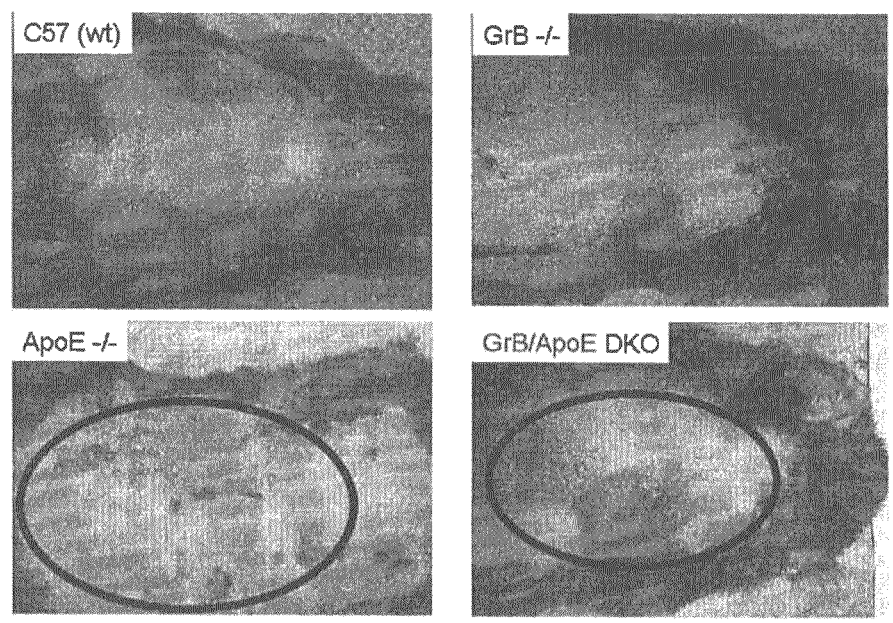
FIG. 6 Skin of dehaired mice. C57 BL/6 (wt), GrB -/-, ApoE -/- and GrB/ApoE double knockout mice (DKO) with hair removed show the varying skin conditions associated with the gene knockout phenotypes.

The skin of ApoE-/- mice appears much more aged, unhealthy and is very fragile. The skin has markedly reduced elasticity, which is restored in the DKO mice, where granzyme B activity is absent (FIG. 6).

Figure 7:
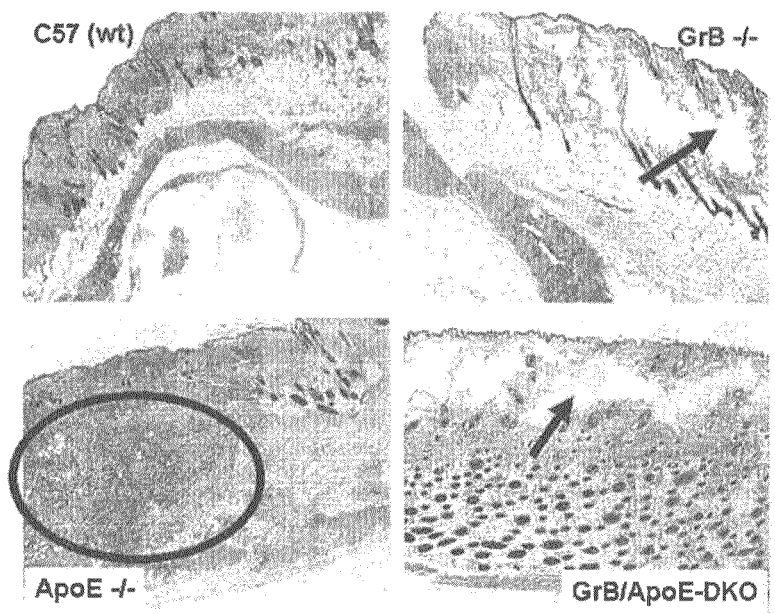
FIG. 7 Representative skin samples at 30 weeks. Hair follicles are deeply embedded in both the GrB-KO and GrB/ApoE-DKO. Hair follicle density is also much greater In the GrB/ApoE DKO. Xanthoma formation is visible in the ApoE-KO and absent from GrB/ApoE-DKO. There also appears to be a change in the extracellular matrix composition in the GrB-KO and DKO mice as the white area/processing artifact is always present in these tissues in the dermis and likely due to changes in hydrophobicity in the matrix and fixation procedures.

In FIG. 7, an area of massive immune cell infiltration in the ApoE-/- mice (circled area) is visible, that is not observed in the DKO mice.

This immune cell recruitment and inflammatory response may be a consequence of the chemotactic action of the cleaved extracellular matrix components such as elastin fragments and fibronectin fragments. The presence of granzyme B in the ApoE-/- mice localizes to these sites and may be contributing to the generation of these fragments. This inflammatory effect (and granzyme B localization) is not observed in the DKO mice.

Additionally, granzyme B may contribute to matrix degradation and/or remodeling of matrix composition, as areas are "lost" or left unstained in the fixation process of tissues from GrB-/- or DKO mice. Granzyme B mediated degradation of matrix, in the presence of high lipids (as observed in the ApoE-/- mice) may contribute to the phenotype observed.

Example 4

Granzyme B Binds to the Extracellular Matrix Protein Elastin

An in vitro granzyme B elastin binding assay was conducted in the following manner. Granzyme B at 50, 100 and 300 ng was incubated with 15 μg of human insoluble skin (Sk) and aortic (Ao) elastin (Elastin Products Company Owensville, Mo.) in PBS for three hours at room temperature. The samples were centrifuged at 1000×g at room temperature for three minutes and the insoluble elastin collected in the pellet. The supernatants, which contained unbound granzyme B, were denatured with SDS loading buffer and run on a 10% SDS-PAGE gel. Granzyme B was detected by Western blot. Each gel contained three lanes: a first lane related to a sample containing granzyme B in the absence of elastin; a second lane related to the samples containing granzyme B and human insoluble skin elastin; and a third lane related to the sample containing granzyme B and aortic elastin. The lane relating to the sample containing granzyme B in the absence of elastin showed a heavy band in the supernatant and a faint band in the pellet. The lanes relating to the samples containing granzyme B and skin elastin, and granzyme B and aortic elastin both showed heavy bands in the pellet, which bands were much heavier than the faint band seen in the pellet relating to the sample containing granzyme B in the absence of elastin. Furthermore, the band in the supernatant for the sample containing granzyme B and skin elastin was dramatically less pronounced than the supernatant band shows in the sample relating to granzyme B in the absence of elastin. No band appeared in the supernatant sample containing granzyme B and aortic elastin. Hence, there is less granzyme B present in the supernatant, thus indicating that granzyme B was associating with the elastin in the pellet. This phenomenon was dose-dependent and not restricted to the type of elastin used (i.e. shin elastin or aortic elastin).

Example 5

Granzyme B Cleaves Extracellular Matrix Proteins

Treatment of human coronary artery smooth muscle cells (SMC) matrix with granzyme B induced a cleavage of a number of extracellular proteins. Extracellular proteins from SMC cultures were biotinylated and incubated with granzyme B. The supernatant was collected at 2, 4 and 24 hours after treatment, and the entire insoluble extracellular protein preparation collected at 24 hours. Extracellular proteins were visualized by Western blot for biotin. Western blot for beta-actin confirmed that the extracellular protein preparation was devoid of intercellular proteins. Western blots for fibronectin, phosphorylated FAK (p-FAK), and FAK. were also performed on lysates of SMC treated with granzyme B. In the collected insoluble proteins, four protein bands between approximately 50-70 kDa and approximately 236 kDa disappeared 24 hours after treatment with granzyme B and cleavage of fragments approximately 25-39 kDa were evident in the matrix at this same time point. Further, the six proteins and/or cleavage fragments ranging in molecular weight from approximately 29-148 kDa were eluted into the supernatant as early as two hours after granzyme B treatment. To ensure that the SMC extracellular protein preparations used were devoid of intracellular proteins, western blotting for beta-actin was performed on the collected supernatant and extracellular proteins. Beta-actin was apparent in SMC lysates (positive control) but was absent from matrix and supernatant preparations.

To identify extracellular proteins that are cleaved by granzyme B, western blots for fibronectin, collagen, and vitronectin on lysates from untreated and granzyme B-treated SMCs were performed. In all SMCs treated with granzyme B for 24 hours, there was a reduction in the total amount of fibronectin in lysates collected from SMCs. In the supernatants of granzyme B-treated SMCs at 24 hours, a fibronectin cleavage product was detected. There was no cleavage of collagen IV or vitronectin was observed. Therefore, granzyme B induces a cleavage of fibronectin in SMC extracellular matrixes but does not affect collagen IV or vitronectin.

Also human coronary artery smooth muscle cells were cultured to confluency and serum starved for 48 hours at which time cells were lysed with NH4OH so that the intact extracellular matrix (ECM) remained on the plate. Granzyme B (80 nm) was incubated on the ECM for 24 hours at room temperature. Supernatants (containing cleaved ECM) and ECM still attached to the plate were collected and assessed for fibrillin cleavage by Western blot. The results, not shown, may be summarized as follows: Western blots of PBS (negative control), Trypsin (positive control) and GrB supernatants and PBS, Trypsin and GrB ECMs were performed with a fibrillin-1 antibody, which showed fibrillin-1 cleavage fragments in the GrB supernatant, GrB ECM, Trypsin supernatant and Trypsin ECM, but not in the PBS supernatant or ECM. Six independent experiments were carried out and 3 representative groups were tested. Results confirm that GrB cleaves fibrillin-1 in human coronary artery smooth muscle cells.

Example 6

Granzyme B Binds and Degrades Elastin In Vitro

Figure 11:
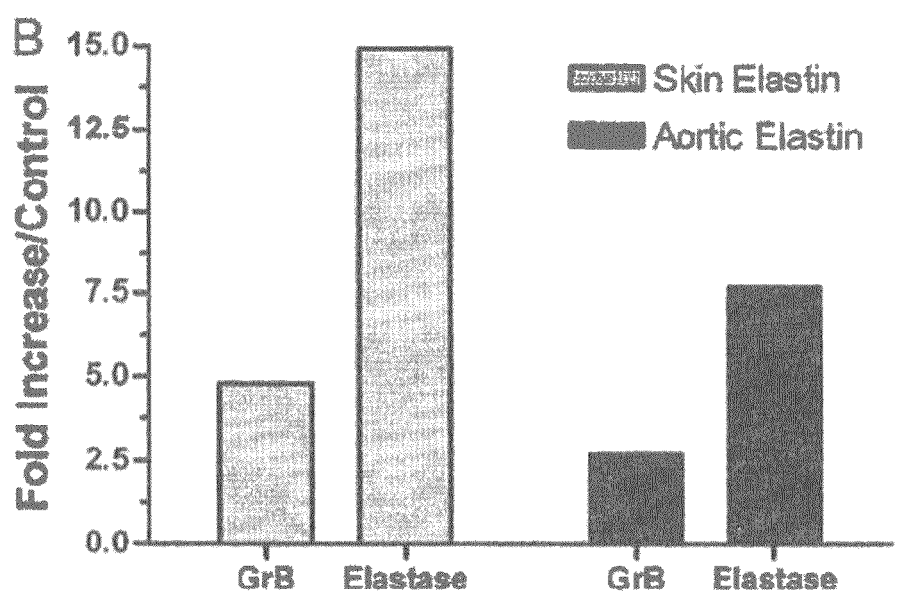
FIG. 11 granzyme B degrades elastin in vitro. Granzyme B was incubated with $^3$H-elastin for 7 days at room temperature. Elastase was incubated with $^3$H-elastin for 2 hours. Supernatants containing the soluble elastin cleavage fragments were collected and counted. Data is represented as fold increase in radioactivity over the control (elastin only). (n=2)

Tritiated elastin was prepared with the modifications as described in Banda, M. J. and Werb, Z. (1981) *Biochem J* 193:589-605 and Gordon, S., Werb, Z. and Cohn, Z. A. (1976) in *In Vitro Methods in Cell Mediated and Tumor Immunity*, eds. Bloom, B. R. and David, J. R. (Academic Press, New York), pages 349-350. 1 mg of skin or aortic elastin was diluted in 1 ml $dH_2O$ and pHed to 9.2. 1 mCi $NaB_3H_4$ (PerkinElmer, Waltham, Mass.) and 2 mg of non-radioactive $NaB_3H_4$ (Sigma, St. Louis, Mo.) was added. After 2 hours of incubation, the pH was adjusted to 3.0 and the elastin was incubated for an additional 30 minutes. The elastin was centrifuged for 3 minutes at 5000×g and the pellet was repeatedly washed to remove excess $NaB_3H_4$. For the cleavage assays, 0.15 mg 3H-elastin was incubated with granzyme B (0.75 µg was added a total of 5 times) at room temperature for 7 days. At day 7 of incubation, 25 µg of elastase (Elastin Products Company, Owensville, Mo.) was incubated with elastin for 2 hours, as a positive control. After incubations, reactions were centrifuged at 5000×g for 3 minutes. The radioactivity of the soluble, cleaved elastin fragments in the supernatant was counted in Ready Safe Scintillation Fluid (Beckman-Coulter, Fullerton, Calif.). The radioactivity of the cleaved, soluble elastin fragments was 4.8 times and 2.7 times higher than background for skin and aortic elastin, respectively (FIG. 11). Proteolysis of elastin by elastase yielded a radioactivity increase over background of 14.9 fold for skin elastin and 7.7 fold for aortic elastin. These data show that granzyme B has affinity to elastin and has elastolytic activity.

Example 7

Whole Blood Plasma Protocol 7.5 ml blood samples were collected from normal subjects (GOLD 1 & 2) and from subject having chronic obstructive pulmonary disease (GOLD 3 & 4) using a purple top EDTA vacutainer tube (BD). Immediately upon collection, the tube was inverted 5 times for thorough mixing. The tubes were then centrifuge for 11 min at 276×g (Beckman Coulter). Following centrifugation, the tubes are separated into 3 distinct layers: a bottom layer of mostly red blood cells, a thin film layer of white blood cells (buffy coat) and a top layer of plasma. Using a sterile transfer pipette, the top layer of plasma down to about 1 mm from the red blood cells was removed, being careful not to aspirate the buffy coat, and the plasma was placed into a labeled orange top cryotube. The samples were stored immediately at −80° C. until plasma analysis was performed.

Granzyme B Analyses Using ELISA Kits From Bender Medsystems

For plasma analysis, human Granzyme B ELISA kits were used (catalog number: BMS2027). The kits comprise enzyme-linked immunosorbent assay for quantitative detection of human granzyme B. The reagents were prepared as per the kit's protocols: a) Wash Buffer; b) Dilution Buffer; c) Biotin-Conjugate; d) Granzyme standards; e) Streptavidin-HRP; and f) Colour-giving reagents: Blue-Dye, Green-Dye, Red-Dye.

Figure 8:
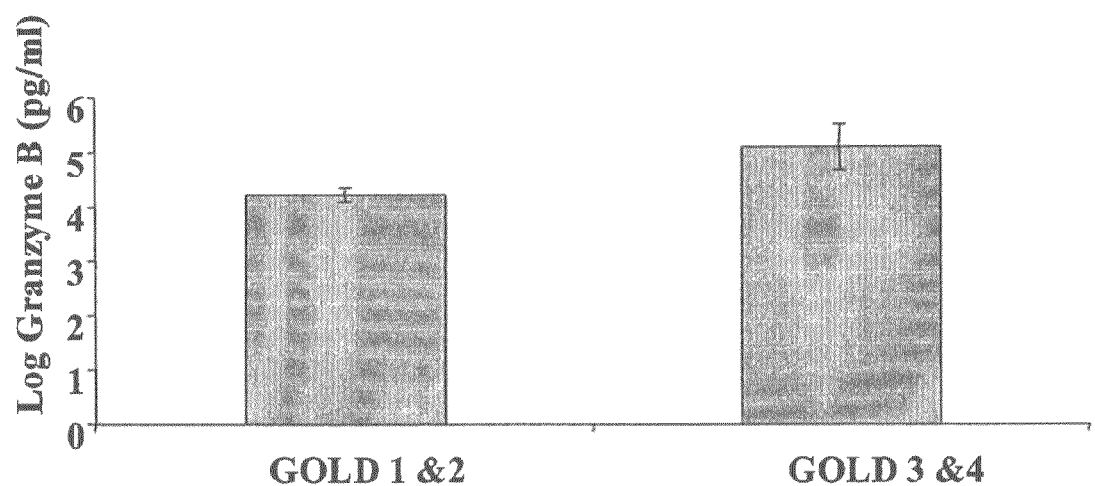
FIG. 8 is a bar graph showing the Log of Granzyme B levels (pg/ml) of two distinct subject groups: GOLD 1 & 2 are a normal subject group and Gold 3 & 4 are a subject group having chrome obstructive pulmonary disease (COPD).
Figure 9:
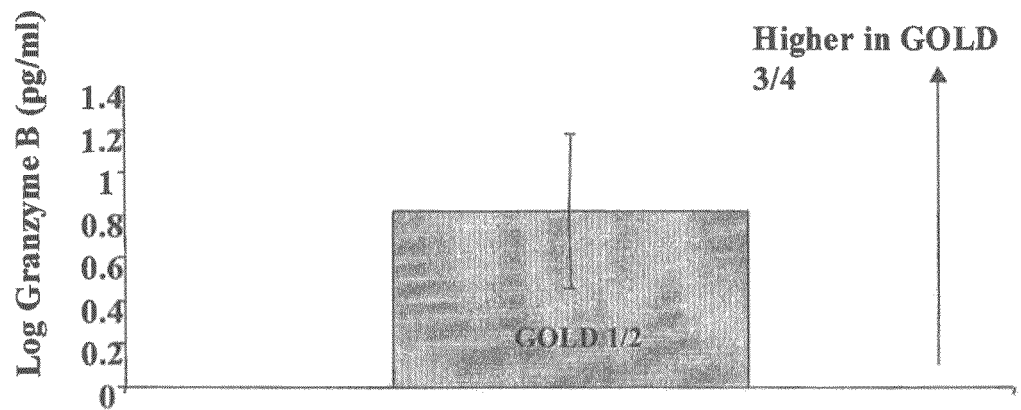
FIG. 9 is a bar graph showing the Log of Granzyme B levels (pg/ml), when adjusted for age and smoking status of two distinct subject groups; GOLD 1 & 2 are a normal subject group and Gold 3 & 4 are a subject group having COPD.
Figure 10:
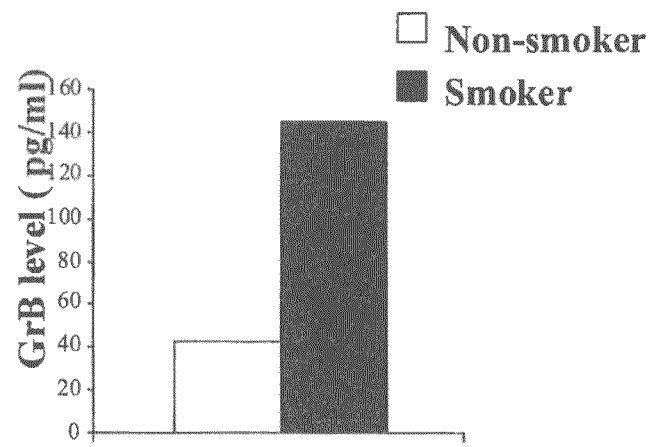
FIG. 10 is a bar graph comparing granzyme B levels in two subject groups: smokers and non-smokers. N=3 for both subject groups.

The assays were performed as per the kit's protocols and the calculation of the results were performed as per the kit's protocols. The results are depicted graphically in FIGS. 8, 9 and 10 and in Table 3 below.

TABLE 3

Granzyme B in the lung

|  |  | GRB [pg/ml] | GRB/Protein [pgGRB/mgProtein] |
|---|---|---|---|
| WL | COPD (n = 3) | 4090.47 | 514.93 |
|  | Control (n = 2) | 1201.94 | 212.36 |
| Cyt | COPD (n = 3) | 3559.18 | 346.66 |
|  | Control (n = 2) | 1072.52 | 140.57 |
| M | COPD (n = 3) | 57.33 | 58.77 |
|  | Control (n = 2) | 7.80 | 8.26 |

Normal (Control) or COPD-afflicted lungsections were isolated. Protein levels of Granzyme B in whole lysates (WL), cytosol (Cyt) or microsomes (M) were assessed using ELISA.

Example 8

Whole Blood Plasma Protocol 7.5 ml blood samples were collected from normal subjects and from subject having chronic obstructive pulmonary disease using a purple top EDTA vacutainer tube (BD). Immediately upon collection, the tube was inverted 5 times for thorough mixing. The tubes were then centrifuge for 11 min at 276×g (Beckman Coulter). Following centrifugation, the tubes are separated into 3 distinct layers: a bottom layer of mostly red blood cells, a thin film layer of white blood cells (buffy coat) and a top layer of plasma. Using a sterile transfer pipette, the top layer of plasma down to about 1 mm from the red blood cells was removed, being careful not to aspirate the buffy coat, and the plasma was placed into a labeled orange top cryotube. The samples were stored immediately at −80° C. until plasma analysis was performed.

Granzyme A Analyses using ELISA Kits from Bender Medsystems

For plasma analysis, human Granzyme A ELISA kits were used (catalog number: BMS2026). The kits comprise enzyme-linked immunosorbent assay for quantitative detection of human granzyme A. The reagents were prepared as per the kit's protocols: a) Wash Buffer; b) Dilution Buffer; c) Biotin-Conjugate; d) Granzyme standards; e) Streptavidin-HRP; f) TMB substrate solution; and g) Colour-giving reagents: Blue-Dye, Green-Dye, Red-Dye.

Figure 12:
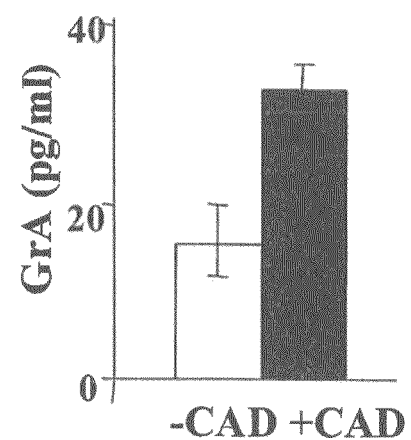
FIG. 12 is a bar graph illustrating the that granzyme A is elevated in the plasma of patients with confirmed atherosclerosis. Plasma samples were obtained from patients with (n=5) or without (n=5) coronary artery disease (CAD).
Figure 13:
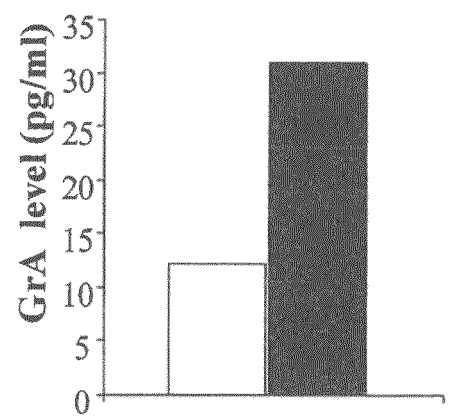
FIG. 13 is a bar graph illustrating the that granzyme A is elevated in the plasma of patients that smoke. Plasma samples were obtained from patients that do (black bar; n=3) or do not (white bar; n=3) smoke.

The assays were performed as per the kit's protocols and the calculation of the results were performed as per the kit's protocols. The results are depicted graphically in FIGS. 12 and 13. FIG. 12 illustrates the results whereby granzyme A is elevated in the plasma of patients with confirmed atherosclerosis. Plasma samples were obtained from patients with (n=5) or without (n=5) coronary artery disease (CAD) from the Healthy Heart Clinic at St. Paul's Hospital in Vancouver, British Columbia, Canada. CAD was determined by angiography and granzyme A levels were measured as described above. FIG. 13 illustrates the results whereby granzyme A levels are elevated in the plasma of patients that smoke. Plasma samples were obtained from patients that do (n=3) or do not (n=3) smoke. Samples were obtained from the Health Heart Clinic at St. Paul's Hospital, in Vancouver, British Columbia, Canada. Plasma levels of granzyme A were measured as described above.

Example 9

Figure 14:
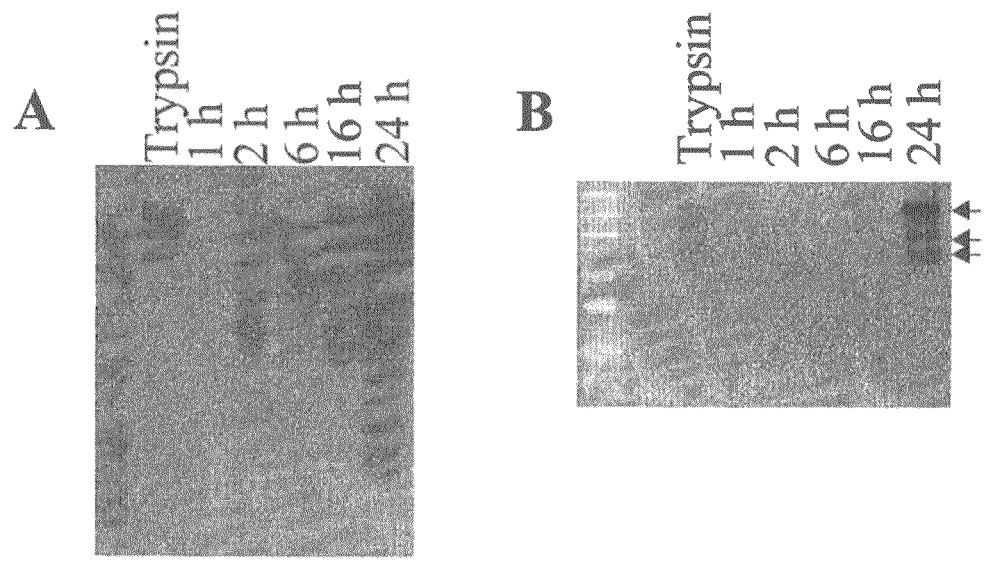
FIG. 14A illustrates extracellular proteins visualized by Western blot for biotin. Increased levels of fragmented extracellular matrix proteins were observed in granzyme A-treated plates.
FIG. 14B illustrates supernatants treated with granzyme A for the indicated times were probed for fibronectin and several fragments were observed, as indicated by the arrows, by Western blot.

Granzyme A-mediated proteolysis of smooth muscle cell (SMC)-generated extracellular proteins is illustrated in FIGS. 14A and 14B. SMC were cultured until confluency and then lysed with 0.25 M $NH_4OH$ for 30 min. The remaining extracellular matrix proteins were biotinylated and incubated with granzyme A. Supernatants were collected at 1, 2, 6, 16 and 24 h post-treatment. FIG. 14A illustrates the results whereby extracellular proteins were visualized by Western blot for biotin. Increased levels of fragmented extracellular matrix proteins were observed in granzyme A-treated plates. FIG. 14B illustrates the results whereby supernatants treated with granzyme A for the indicated times were probed for fibronectin and several fragments were observed as indicated by the arrows.

Granzyme A cleaves fibrillin-1 in vitro. Human coronary artery smooth muscle cells were cultured to confluency and serum starved for 48 hours at which time cells were lysed with $NH_4OH$ so that the intact extracellular matrix (ECM) remained on the plate. Granzyme A (100 nM) in PBS was incubated on the ECM for 24 hours at room temperature. Supernatants were collected and assessed for fibrillin presence and size by SDS-PAGE and Subsequent fibrillin-1 Western blot (results not shown). The results, may be summarized as Follows: Western blots of PBS (negative control), Trypsin (positive control) and GrA supernatants and PBS, Trypsin and GrA ECMs were performed with a fibrillin-1 antibody, which showed fibrillin-1 cleavage fragments in the GrA supernatant, GrA ECM, Trypsin supernatant, and Trypsin ECM, but not in the PBS supernatant or ECM. Six independent experiments were carried out and 3 representative groups were tested. Results confirm that GrA cleaves fibrillin-1 in human coronary artery smooth muscle cells. Furthermore, GrB has also been shown to cleave Fibrillin-2 and Fibulin-2 in human coronary artery smooth muscle cells (HCASMC)-derived ECM (data not shown) and GrB cleavage is attenuated by the granzyme B inhibitor dichloroisocoumarin (DCI).

The invention claimed is:

1. A method of diagnosis of a fibrillinopathy in a subject suspected of having fibrillinopathy or having a fibrillinopathy, the method comprising:
   a) determining a concentration of GrB (Granzyme B) in a blood plasma or serum sample from said subject; and
   b) comparing said concentration to a corresponding concentration in a control sample, wherein an elevated concentration of GrB is indicative of fibrillinopathy.

2. The method of claim 1, further comprising determining a concentration of one or more of: elastin, and fibrillin; with reference to said control sample is indicative of fibrillinopathy.

3. The method of claim 1, wherein the concentration of GrB is determined by an immunodiagnostic assay.

4. The method of claim 2, wherein the concentration of elastin or fibrillin is determined by an immunodiagnostic assay.

5. The method of claim 3 or 4, wherein the immunodiagnostic assay is an enzyme-linked immunosorbent assay (ELISA).

6. The method of claim 1, wherein the fibrillinopathy is selected from one of more of: Marfan Syndrome, Beal's syndrome, congenital contractural arachnactyly, supravalvular aortic stenosis, Williams-Beuren syndrome, autosomal recessive cutis laxa, autosomal dominant cutis laxa, and acquired cutis laxa.

7. The method of claim 1, wherein the subject has a GrB blood plasma concentration of >40 pg/ml.

8. The method of claim 2, wherein the elastin or fibrillin, may be an elastin degradation product or a fibrillin degradation product.

9. The method of claim 1, further comprising one or more of: diagnostic imaging, clinical diagnosis and alternative laboratory diagnostics.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Mus musculus

<400> SEQUENCE: 1
tgaagatcct cctgctactg c                                            21

<210> SEQ ID NO 2
<211> LENGTH: 20
<212> TYPE: DNA
<213> ORGANISM: Mus musculus

<400> SEQUENCE: 2
tcctgagaaa gacctctgcc                                              20

<210> SEQ ID NO 3
<211> LENGTH: 20
<212> TYPE: DNA
<213> ORGANISM: Mus musculus

<400> SEQUENCE: 3
gcctagccga gggagagccg                                              20

<210> SEQ ID NO 4
<211> LENGTH: 22
<212> TYPE: DNA
<213> ORGANISM: Mus musculus
```

-continued

```
<400> SEQUENCE: 4
tgtgacttgg gagctctgca gc                                        22
```